United States Patent
Kulp et al.

(10) Patent No.: US 7,151,787 B2
(45) Date of Patent: Dec. 19, 2006

(54) BACKSCATTER ABSORPTION GAS IMAGING SYSTEMS AND LIGHT SOURCES THEREFORE

(75) Inventors: Thomas Jan Kulp, Livermore, CA (US); Dahv A. V. Kliner, San Ramon, CA (US); Ricky Sommers, Oakley, CA (US); Uta-Barbara Goers, Campbell, NY (US); Karla M. Armstrong, Livermore, CA (US)

(73) Assignee: Sandia National Laboratories, Livermore, CA (US)

( * ) Notice: Subject to any disclaimer, the term of this patent is extended or adjusted under 35 U.S.C. 154(b) by 199 days.

(21) Appl. No.: 10/658,906

(22) Filed: Sep. 10, 2003

(65) Prior Publication Data

US 2005/0053104 A1 Mar. 10, 2005

(51) Int. Cl.
*H01S 3/091* (2006.01)
(52) U.S. Cl. .......................... 372/70; 372/20; 372/22; 372/6
(58) Field of Classification Search .................... 372/6, 372/20, 21, 22, 70
See application file for complete search history.

(56) References Cited

U.S. PATENT DOCUMENTS

| | | | |
|---|---|---|---|
| 3,609,398 A | 9/1971 | Bjorkholm | 307/88.3 |
| 3,628,186 A | 12/1971 | Rumson et al. | 331/107 R |
| 3,948,345 A | 4/1976 | Rosencwaig | 181/0.5 |
| 4,555,627 A | 11/1985 | McRae, Jr. | |
| 4,622,845 A | 11/1986 | Ryan et al. | 73/24 |
| 4,745,276 A | 5/1988 | Broicher et al. | |
| 5,097,477 A * | 3/1992 | Scheps | 372/94 |
| 5,117,126 A | 5/1992 | Geiger | 359/330 |
| 5,202,560 A | 4/1993 | Kock et al. | 356/435 |
| 5,430,293 A | 7/1995 | Sato et al. | |
| 5,434,700 A | 7/1995 | Yoo | |
| 5,656,813 A | 8/1997 | Moore et al. | |
| 5,864,644 A | 1/1999 | DiGiovanni et al. | |

(Continued)

FOREIGN PATENT DOCUMENTS

EP  0 857 997 B1  10/2001

(Continued)

OTHER PUBLICATIONS

Goers et al., Development of a compact gas imaging sensor employing a cw fiber-amp pumped PPLN OPO technical paper during CLEO 2001 sent in by IDS on Oct. 20, 2003.*

(Continued)

*Primary Examiner*—Minsun Oh Harvey
*Assistant Examiner*—Dung (Michael) T. Nguyen
(74) *Attorney, Agent, or Firm*—Steven R. Vosen (57) ABSTRACT

The location of gases that are not visible to the unaided human eye can be determined using tuned light sources that spectroscopically probe the gases and cameras that can provide images corresponding to the absorption of the gases. The present invention is a light source for a backscatter absorption gas imaging (BAGI) system, and a light source incorporating the light source, that can be used to remotely detect and produce images of "invisible" gases. The inventive light source has a light producing element, an optical amplifier, and an optical parametric oscillator to generate wavelength tunable light in the IR. By using a multi-mode light source and an amplifier that operates using 915 nm pump sources, the power consumption of the light source is reduced to a level that can be operated by batteries for long periods of time. In addition, the light source is tunable over the absorption bands of many hydrocarbons, making it useful for detecting hazardous gases.

90 Claims, 5 Drawing Sheets

U.S. PATENT DOCUMENTS

| | | | |
|---|---|---|---|
| 6,157,033 | A | 12/2000 | Chudnovsky |
| 6,229,828 | B1* | 5/2001 | Sanders et al. ............... 372/22 |
| H1965 | H | 6/2001 | Burns et al. .................. 372/22 |
| 6,304,237 | B1* | 10/2001 | Karakawa ..................... 345/84 |
| 6,324,326 | B1* | 11/2001 | Dejneka et al. ............. 385/123 |
| 6,344,647 | B1 | 2/2002 | Jourdain et al. ....... 250/339.07 |
| 6,359,914 | B1 | 3/2002 | Powers et al. |
| 6,455,854 | B1 | 9/2002 | Richman |
| 6,751,010 | B1* | 6/2004 | Richter ....................... 359/330 |
| 6,757,096 | B1 | 6/2004 | Schiller ...................... 359/330 |
| 6,813,429 | B1 | 11/2004 | Price et al. ................. 385/125 |
| 2003/0081192 | A1* | 5/2003 | Nishi .......................... 355/69 |
| 2004/0006276 | A1* | 1/2004 | Demos et al. ............... 600/476 |
| 2004/0036957 | A1* | 2/2004 | Galvanauskas et al. .. 359/341.3 |

FOREIGN PATENT DOCUMENTS

| | | |
|---|---|---|
| WO | WO 98/01927 | 1/1998 |
| WO | WO 02/27297 A1 | 4/2002 |

OTHER PUBLICATIONS

Goers et al. (Development of a compact gas imaging sensor employing a cw fiber-amp-pumped PPLN OPO Technical Paper in CLEO 2001).*

Optics Letters, vol. 21, No. 17; Bosenberg, et al., "*93% pump depletion, 3.5-W continuous-wave, singly resonant optical parametric oscillator,*" pp. 1336-1338, Sep. 1, 1996.

Springer-Verlag; Applied Physics B, Lasers and Optics; D.G. Lancaster, et al.; "*Portable fiber-coupled diode-laser-based sensor for multiple trace gas detection;*" pp. 459-465; Rice University, Houston, TX., Jun. 24, 1999.

CLEO 2001 Conference; Goers, et al., "*Development of a compact gas imaging sensor employing a cw fiber-amp-pumped PPLN OPO,*" Baltimore, MD, May 6-11, 2001.

M. J. T. Milton and P. T. Woods, "Pulse averaging methods for a laser remote monitoring system using atmospheric backscatter," Applied Optics, 26, No. 13, 2598 (1987).

N. Menyuk, D. K. Killinger, and C. R. Menyuk, "Limitations of signal averaging due to temporal correlation in laser remote-sensing measurements," Applied Optics, 21, No. 18, 3377 (1982).

T. G. McRae and T. J. Kulp, "Backscatter absorption gas imaging: a new technique for gas visualization," Applied Optics, 32, No. 21, 4037 (1993).

T. J. Kulp, P. Powers, R. Kennedy, and U. Goers, "Development of a pulsed backscatter-absorption gas-imaging system and its application to the visualization of natural gas leaks," Applied Optics, 37, No. 18, 3912 (1998).

Gregory David Miller, "Periodically Poled Lithium Niobate: Modeling, Fabrication, and Nonlinear-Optical Performance", Ph.D. Dissertation, Stanford University, Jul. 1998.

L. Goldberg, J. Koplow, D. G. Lancaster, R. F. Curl, and F. K. Tittel, "Mid-infrared difference-frequency generation source pumped by a 1.1-1.5 μm dual-wavelength fiber amplifier for trace-gas detection", *Optics Letters,* vol. 23, No. 19, Oct. 1, 1998, pp. 1517-1519.

D. G. Lancaster, D. Richter, R. F. Curl, F. K. Tittel, L. Goldberg, and J. Koplow, "High-Power continuous-wave mid-infrared radiation generated by difference frequency mixing of diode-laser-seeded fiber amplifiers and its application to dual-beam spectroscopy", *Optics Letters,* vol. 24, No. 23, Dec. 1, 1999, pp. 1744-1746.

H. Dahnke, D. Kleine, P. Hering, and M. Mürtz, "Real-time monitoring of ethane in human breath using mid-infrared cavity leak-out spectroscopy", *Appl. Phys. B 72,* May 9, 2001, pp. 971-975.

Naoya Matsuoka, Shigeru Yamaguchi, Kenzo Nanri, Tomoo Fujioka, Dirk Richter and Frank K. Tittel, "Yb Fiber Laser Pumped Mid-IR Source Based on Difference Frequency Generation and Its Application to Ammonia Detection", *Jpn. J. Appl. Phys.,* vol. 40, Part 1, No. 2A, Feb. 2001, pp. 625-628.

Uta-Barbara Goers, Karla Armstrong, Ricky Sommers, Thomas J. Kulp, Dahv A.V. Kliner, Sal Birtola, Lew Goldberg, Jeffrey P. Koplow, and T.G. McRae, "Development of a compact gas imaging sensor employing a cw fiber-amp-pumped PPLN OPO", Presentation at CLEO, Apr. 2001.

Scott E. Bisson, Karla A. Armstrong, Thomas J. Kulp, and Matthew Hartings, "Broadly tunable, mode-hop-tuned cw optical parametric oscillator based on periodically poled lithium niobate", *Applied Optics,* vol. 40, No. 33, Nov. 20, 2001, pp. 6049-6055.

CDRL Report No. A009, "Commercialization of Technologies to Lower Defense Costs, Draft Laser-Based Sensors for VOCs, Technology Assessment", 19 pages, Mar. 22, 2002.

"Construction of CW Optical Parametric Oscillators", http//www.nat.vu.nl/vakgroepen/atom/english/research/appspec/opos.html, Aug. 15, 2002.

SERDP Fact Sheet, "Sensors for VOC/NOx and Metal Particulate Emissions Monitoring", Mar. 25, 1999.

\* cited by examiner

BACKSCATTER ABSORPTION GAS IMAGING SYSTEMS AND LIGHT SOURCES THEREFORE

STATEMENT REGARDING FEDERALLY SPONSORED RESEARCH OR DEVELOPMENT

This invention was made with Government support under contract No. DE-AC04-94AL85000 awarded by the U.S. Department of Energy to Sandia Corporation. The Government has certain rights in the invention.

FIELD OF THE INVENTION

The present invention relates generally to light sources and systems for gas detection systems, and more particularly, to wavelength tunable light sources and gas imaging systems employing tunable light source.

BACKGROUND OF THE INVENTION

Most gases are invisible to the unaided human eye, particularly at low concentrations. It is thus difficult, and sometimes impossible, to visually determine the presence and extent of releases of these gas into the environment. The ability to rapidly detect and track hazardous gases in the atmosphere would greatly aid public safety and health, and would be useful and in determining the source of gaseous leaks in general. For example, accidental toxic or combustible gas releases can occur from malfunctioning industrial equipment or from accidents involving the transport of bulk hazardous materials. These releases can rapidly diffuse into the surrounding air and move with the prevailing wind. While the safety of the public would be greatly enhanced in such circumstances by the easy determination of the location, extent, and motion of these gases, there is no device that is capable of providing this information.

The detection of leaks is of concern in industrial settings. For example, the natural gas and petroleum industries are mandated by law to regularly perform leak surveillance of their processing hardware and product pipelines. Existing detection technology is labor intensive and costly, requiring manually use of equipment that measures at a single point and in close proximity to the leak source. Leak inspections thus require approaching within 1 cm of tens of thousands of potential leak points per facility. In addition, point measurements of gas concentration do not provide information on the volume of release, and are of limited use in quantifying the amount of gas in a leak.

Backscatter absorption gas imaging (BAGI) is one advanced technique that shows promise for remotely producing real-time video images of otherwise invisible gases. A BAGI system consists of a light source that produces radiation that is absorbed by a gas of interest and a video camera that collects the light to produce images of the extent of the gas within an imaged scene. Specifically, light is directed to illuminate an area having a solid object (e.g., a wall) in the camera's field of view. The solid object scatters light back towards the camera, and if the gas of interest is present, it will absorb the backscattered light. Light that is thus backscattered is imaged, or processed to produce an image, of the scene that can be interpreted by the BAGI system user to determine the presence and position of gas in the environment. A BAGI image, for example, can consist of light and dark regions according to the amount of absorbing gases present. Brighter regions correspond to scenes having no, or small amounts of, absorbing gases, and darker regions correspond to scenes having higher amounts of absorbing gases. By adjusting the wavelength of the BAGI light source to correspond to the absorption of different gases, BAGI systems can produce images of the extent of these different gases.

The camera of a BAGI system thus produces an image of source light that is backscattered to the camera from solid surfaces in the scene of the camera field-of-view. As such, BAGI is limited to producing images of scenes containing a solid surface.

Prior art BAGI systems suffer from limitations that prevent them from being generally useful in producing real-time video images of gas in the environment. In particular, a useful BAGI system should have a light source that is 1) easily adjustable to provide light that is both transmitted through the atmosphere and absorbed by gases of interest, 2) has an output power high enough to enable measurements to be made at a distance, and 3) have low power consumption so the system can be portable. Prior art systems do not meet all of these requirements. In particular, no BAGI system exists that meets these requirements for imaging hydrocarbon gases. Another requirement for a useful BAGI system is compatibility with common and inexpensive cameras. This requirement is met with a light source that emits light compatible with scanning cameras. Pulsed format BAGI systems are not compatible with these cameras.

The lack of BAGI instrumentation that can address particular market needs has significantly impacted the size of the available market for BAGI instrumentation and has deprived certain industries of the benefits of the technology. For example, the petroleum industry is mandated to perform leak detection on a quarterly basis at each of their processing refineries. This is currently done using manually-positioned probes that must be placed in close proximity to thousands of potential leak points during a survey. A typical large refinery spends approximately $1,000,000 per year in leak detection and repair activities. The petroleum industry has recognized the potential of gas imaging as a means to perform these operations more rapidly. The American Petroleum Institute (API) recognizes gas imaging as a means to satisfy their goal of Smart Leak Detection and Repair (Smart LDAR). Prior to the invention described in this document, however, BAGI could not meet this need due to the lack of instrumentation capable of viewing hydrocarbon leaks, which are the primary emissions at a refinery. Similar unfulfilled needs exist in the natural gas industry, which must perform mandated leak detection operations on natural gas leaks in their pipelines and processing facilities. There, detection of natural gas (primarily methane) is required, which is again not possible with existing BAGI instrumentation. The need for a hydrocarbon-imaging BAGI system has existed for over fifteen years but remains unfulfilled.

The spectral requirements of a BAGI light source can be met with a spectrally-narrow and tunable light source that generates sufficiently powerful radiation in the infrared (IR). Specifically, the needs described in the previous paragraph can be met by illuminating with light in the wavelength range between 3 and 4 μm (frequencies between 2500 and 3333 $cm^{-1}$) as some of these wavelengths correspond with spectroscopic features of hydrocarbon gases and are efficiently transmitted through the atmosphere.

Unfortunately, there is no commercially available, wavelength tunable infrared (IR) light source that meets all of the requirements for a BAGI system suitable for use in hydrocarbon leak detection and, thus, much of the work in developing BAGI systems has been directed to light source development. One light source that can potentially fulfill the needed requirements is the combination of a near-IR light source, such as a laser or diode with output at a wavelength of about 1 μm, that acts as a pump beam for a nonlinear frequency converter with an output in the 3 to 4 μm (2500 to 3333 cm$^{-1}$) range. A range of output wavelengths results from tuning the light source and/or the frequency converter.

Currently available light sources using nonlinear frequency converters have limited utility as a BAGI light source. While these sources generate light of a useful wavelength, tunable near 3.3 μm, the power levels of 200–300 mW are insufficient to operate at distance greater than 2–4 m. In addition, these light sources suffer from other deficiencies that hinder their usefulness in portable devices. These limitations include: unstable light source behavior that varies from day-to-day, less than theoretical tuning range and power in practice, excessive light source cooling requirements, and difficulty in servicing the light source.

In summary, there are no known devices available either in development or in the marketplace that meet the requirements of a BAGI light source suitable for hydrocarbon detection in a useful way.

Therefore, it would be desirable to have a system that provides a portable gas imaging system, and thereby enables the use of gas imaging systems to sense the presence of leaks of hazardous or other visually transparent gases.

SUMMARY OF THE INVENTION

The present invention provides a method for constructing a compact, rugged, broadly-tunable, and laser-illuminated imaging system that is suitable for BAGI.

In one aspect of the present invention, a BAGI system and a light source for a BAGI system is provided having a fiber-based light amplifier.

In another aspect of the present invention, a BAGI system and a light source for a BAGI system is provided that is portable and that is tunable over wavelengths near 3 μm, with a potential for tuning from 1.3 to 4 μm with an adjustment of components.

In yet another aspect of the present invention, a BAGI system and a light source for a BAGI system is provided having a tunable light-generating device, an OFA, and an optical parametric oscillator (OPO). The OPO can either have a fixed operating configuration, or can have a cavity that is tunable.

In one aspect of the present invention, a BAGI system and a light source for a BAGI system is provided having a OPO with a periodically poled lithium niobate (LiNbO$_3$), or PPLN, crystal as a nonlinear material.

In yet another aspect of the present invention, an air-cooled amplifier is provided for a light source and for a light source of a BAGI system. The air-cooled amplifier allows for lower power operation than is available in the prior art.

One aspect of the present invention provides illumination for a scene for a BAGI system including a light-generating device operating at an ambient temperature producing light at more than one wavelength, and optical fiber amplifier, and a nonlinear frequency converter. The optical fiber amplifier has at least one pump laser, accepts light from the light-generating device and produces amplified light at said more than one wavelength. The pump laser is an air-cooled pump laser, and the output of the optical fiber amplifier varies with the temperature of the pump laser. The nonlinear frequency converter includes an OPO to accept the amplified light and generate an output of the light source at wavelengths shifted from and corresponding to each of the more than one wavelength. The optical fiber amplifier also has a gain medium, and the absorption of the pump laser by said gain medium varies by no more than about 10% over a range of ambient temperatures of said light source from about 0 C to about 40 C.

Another aspect of the present invention provides a light source to provide illumination for a scene for a BAGI system including a light-generating device producing light at more than one wavelength, an optical fiber amplifier to accept light from said light-generating device and produce amplified light at said more than one wavelength, where the optical fiber amplifier is a Yb-doped, tapered optical fiber amplifier, an a nonlinear frequency converter including an OPO to accept the amplified light and generate an output of the light source at wavelengths shifted from and corresponding to each of said more than one wavelength. In one embodiment the optical fiber amplifier includes at least one pump laser that is sufficiently air-cooled to provide an amplifier output that varies by no more than 10%.

Yet another aspect of the present invention provides a light source to provide illumination for a scene for a BAGI system including two or more light-generating devices, each producing light at more than one wavelength, a switch to select light from one of the two or more light-generating devices, an optical fiber amplifier to accept said selected light and produce amplified light at the more than one wavelength of said selected light, and an OPO to accept said amplified light and generate an output of the light source at wavelengths shifted from and corresponding to each of said more than one wavelength.

Another aspect of the present invention provides a light source to provide illumination for a scene for a BAGI system comprising a diode-pumped fiber laser producing an output of light at more than one wavelength and a nonlinear frequency converter including an OPO to accept the output and generate an output of the light source at wavelengths shifted from and corresponding to each of said more than one wavelength. The diode-pumped fiber laser is an air-cooled laser, the output varies with temperature, and diode-pumped fiber laser is sufficiently air-cooled to provide an output that varies by no more than 10%.

One aspect of the present invention provides a BAGI system for imaging a gas between the system and a scene comprising a light source and a camera responsive to backscattered illumination by said light source. The light source includes a light-generating device producing light at more than one wavelength, an optical fiber amplifier, and a nonlinear frequency converter. The optical fiber amplifier has at least one pump laser, accepts light from the light-generating device and produces amplified light at said more than one wavelength. The pump laser is an air-cooled pump laser, and the output of the optical fiber amplifier varies with the temperature of the pump laser. The nonlinear frequency converter includes an OPO to accept the amplified light and generate an output of the light source at wavelengths shifted from and corresponding to each of the more than one wavelength. The optical fiber amplifier also has a gain medium, and the absorption of said pump laser by said gain medium varies by no more than about 10% over a range of ambient temperatures of said light source from about 0 C to about 40 C.

Another aspect of the present invention provides a BAGI system for imaging a gas between the system and a scene comprising a light source and a camera responsive to backscattered illumination by said light source. The light source includes a light-generating device producing light at more than one wavelength, an optical fiber amplifier to accept light from said light-generating device and produce amplified light at said more than one wavelength, where the optical fiber amplifier is a Yb-doped, tapered optical fiber amplifier, an a nonlinear frequency converter including an OPO to accept the amplified light and generate an output of the light source at wavelengths shifted from and corresponding to each of said more than one wavelength. In one embodiment the optical fiber amplifier includes at least one pump laser that is sufficiently air-cooled to provide an amplifier output that varies by no more than 10%.

Yet another aspect of the present invention provides a BAGI system for imaging a gas between the system and a scene comprising a light source and a camera responsive to backscattered illumination by said light source. The light source includes two or more light-generating devices, each producing light at more than one wavelength, a switch to select light from one of the two or more light-generating devices, an optical fiber amplifier to accept said selected light and produce amplified light at the more than one wavelength of said selected light, and an OPO to accept said amplified light and generate an output of the light source at wavelengths shifted from and corresponding to each of said more than one wavelength.

One aspect of the present invention provides a BAGI system for imaging a gas between the system and a scene comprising a light source and a camera responsive to backscattered illumination by said light source. The light source includes a diode-pumped fiber laser producing an output of light at more than one wavelength and a nonlinear frequency converter including an OPO to accept the output and generate an output of the light source at wavelengths shifted from and corresponding to each of said more than one wavelength. The diode-pumped fiber laser is an air-cooled laser, and where the output varies with temperature, and where diode-pumped fiber laser is sufficiently air-cooled to provide an output that varies by no more than 10%.

In conjunction with the aspects of the present invention, several embodiments are provided for the elements of the light source and BAGI system. In one embodiment, the light-generating device is continuous-wave, and in another embodiment the light-generating device is quasi-continuous-wave light with a repetition rate greater than about 10 kHz. Light-generating device embodiments also include a multi-longitudinal-mode laser, such as a Nd:YAG laser, a laser diode, and a fiber laser. In yet another embodiment, the light-generating device produces wavelength tunable light, for example light tunable between two wavelengths.

In one embodiment, the optical fiber amplifier is a Yb-doped, tapered fiber amplifier, and preferably the pump laser wavelength operates near 915 nm.

In one embodiment the OPO includes an OPO with a cavity that tunably adjusts said wavelength output. In another embodiment, the OPO accepts the amplified light, generates a signal beam and an idler beam, and the OPO is singly resonant at the wavelength of either said signal beam or of said idler beam. In an alternative embodiment, the OPO is doubly resonant at the wavelength of said signal beam and at the wavelength of said idler beam.

BRIEF DESCRIPTION OF THE DRAWINGS

The foregoing aspects and the attendant advantages of this invention will become more readily apparent by reference to the following detailed description when taken in conjunction with the accompanying drawings wherein.

Reference symbols are used in the Figures to indicate certain components, aspects or features shown therein, with reference symbols common to more than one Figure indicating like components, aspects or features shown therein.

DETAILED DESCRIPTION OF THE INVENTION

The light source of the present invention overcomes the problems associated with prior art light sources for remote gas detection systems, in particular light sources for BAGI systems. More specifically, the present invention provides a light source that can be used for portable gas imaging systems, and can be used, for example, in a battery-operated BAGI system. In addition, the light source of the present invention is more stable and tunable than CW prior art BAGI light sources operating near 3 μm, producing stable light of higher power at a lower electrical power input than is available in the prior art.

Figure 1:
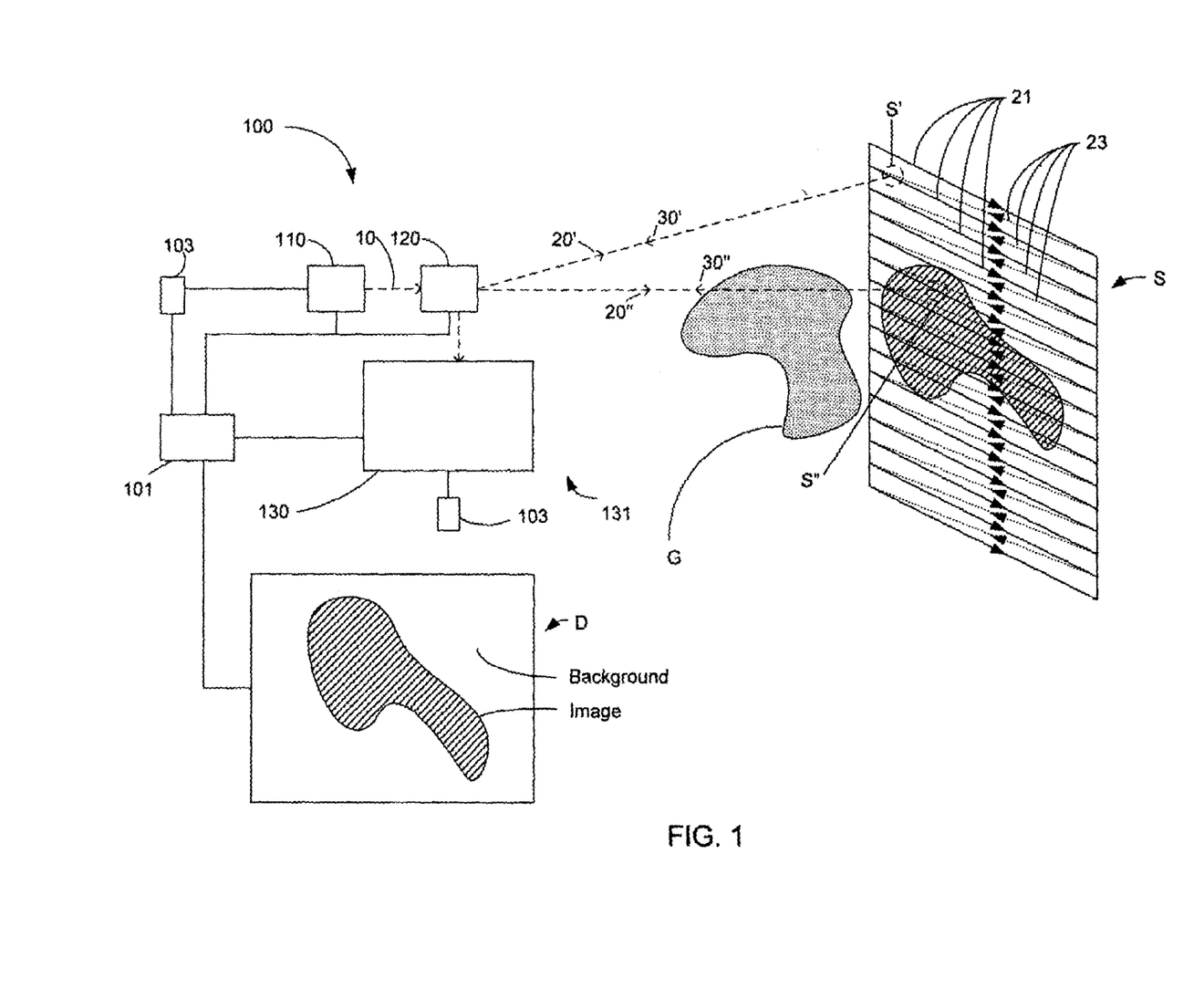
FIG. 1 is a schematic diagram of an embodiment BAGI system of the present invention that includes a source and a raster-scanned detector.

As one example of the light source of the present invention, the light source will now be discussed as being incorporated into a BAGI system. The following discussion is for illustrative purposes and is not meant to limit the scope of the invention. Specifically, FIG. 1 is a schematic of a BAGI system 100 directed towards a gas G and a surface S. As discussed above, the BAGI system detects one or more gases of interest by illuminating a scene with laser light which is absorbed by the gases both in transit to and on reflection from a backscattering surface in the scene. Imaging thus requires that the gases to be imaged are between the BAGI system 100 and a surface S within the imaged scene, and that illumination by the BAGI system occurs at a frequency of light corresponding to an absorption feature of the gases to be imaged. While the present invention is described as imaging gases that are between the BAGI system and a surface, neither the gas G nor the surface S is part of the present invention.

BAGI system 100 includes a light source 110, a scanner 120, an IR detector 130, a computer 101, and one or more batteries 103. Source 110 provides light that is directed to scan surface S by scanner 120. Scanner 120 also scans the instantaneous field-of-view (IFOV) of the IR detector. Thus detector 130 receives light originating from source 110 and that has been backscattered from surface S. Computer 101 controls the wavelength of the light in source 110 and the motion of scanner 120, which both projects the laser beam and controls the IFOV an infrared detector. The computer processes the detector signal to create a raster-scanned, laser-illuminated image of the scene, which can then be used to indicate the presence of gases, as described below. Scanner 120, detector 130, and computer 101 thus function as a raster-scanned camera 131. The computer 101 can either be a single computer performing the functions described below, or can consist of computer processors or other electronic components distributed through BAGI system 100 to perform these functions.

Light source 110, unlike the prior art BAGI light sources, is small, efficient, and has a low power consumption rate. As such, light source 110 provides a BAGI system that can be provided in a self-contained package, and that is portable and rugged enough for field use. Batteries 103 provide all of the electric power for the BAGI system 100, including but not limited to the light source 110, scanner 120, detector 130, and computer 101.

Source 110 produces light, shown as a beam 10, that is directed by scanner 120 as a beam 20 towards surface S for imaging. Source 110, as described in detail below, generates beam 10 at a wavelength and power that is useful for BAGI. Scanner 120 redirects beam 10 and with a moving or rotating mirror, prism, or lens, a solid state device such as an acousto-optic modulator, or other device that can direct beam 10 as beam 20 in a scanned pattern towards surface S, as indicated by reference numbers 21 and 23. As indicated in FIG. 1, a portion of beam 20 is backscattered from surface S towards detector 130, indicated as backscattered light beam 30. Also as indicated in FIG. 1, a portion of the backscattered radiation falls within the IFOV of detector 130. As examples of scanned beam and the IFOV, beams 20 and 30 are shown in FIG. 1 as beam 20' directed at a surface area S' and backscattered to detector 130 as backscattered beam 30', and beam 20" directed at a surface area S" and backscattered laser light to detector 130 as backscattered beam 30".

The frequency of light in beams 10, 20, and 30 is the same, and is selected for its ability to be absorbed by gas G and to not be absorbed by the surrounding air. Importantly, the light produced by source 110 has a narrow spectral distribution, $\Delta v$, about a central frequency $v$. It is preferred that frequency $v$ of beam 10 is adjustable, allowing for tuning of the system to identify the gas species, differentiate between different gas species, and address a wide variety of gaseous species. In addition, it is preferred that the spectral distribution $\Delta v$ is within an absorption band of the gas to be imaged. These features allow BAGI system 100 to be tunable for detection of more than one gaseous species. In one embodiment, source 110 provides for tuning of $v$ with steps of less than 1 $cm^{-1}$ over a broad spectral range of from approximately 2850 to approximately 3150 $cm^{-1}$ or more.

For a given backscattered light intensity, light that does not pass through gas G, for example light beam 30', has a higher intensity than does light that passes through gas G, for example light beam 30". The preferential absorption of backscattered light by gas G thus provides an image on a display D. FIG. 1 shows display D indicating a light shaded background and a dark shaded gas image.

The presentation of backscattered gas images as image on a display D in FIG. 1 is one representation of backscattered gas absorption data, and is not meant to limit the scope of the present invention. In particular, BAGI systems that present or process the backscattered light intensity information differently are within the scope of the present invention. Examples include, but are not limited to: still or moving images on a video monitor, images of processed signals that present false color, gray scales or contours representative of concentration levels, images transmitted via wire or by radio to one or more location remote from the light source and detector, for example as might be convenient in a continuous remote monitoring station for an industrial plant. In addition, BAGI system 100 can collect images at different wavelengths of source light, and the collected images can be processed to spectroscopically speciate the absorbing gases in the image.

As described below, computer 101 has appropriate computing capabilities or interfaces to control the generation of tunable light from source 110, to scan the light on surface S with scanner 120, to acquire images with detector 130 and to generate a display D of a gas image. As noted previously, computer 101 can either be one computer, or can include distributed computers or electronic components that work together. Thus, for example, scanner 120 and detector 130 can include electronic components that communicate therebetween to allow for synchronization.

Figure 2:
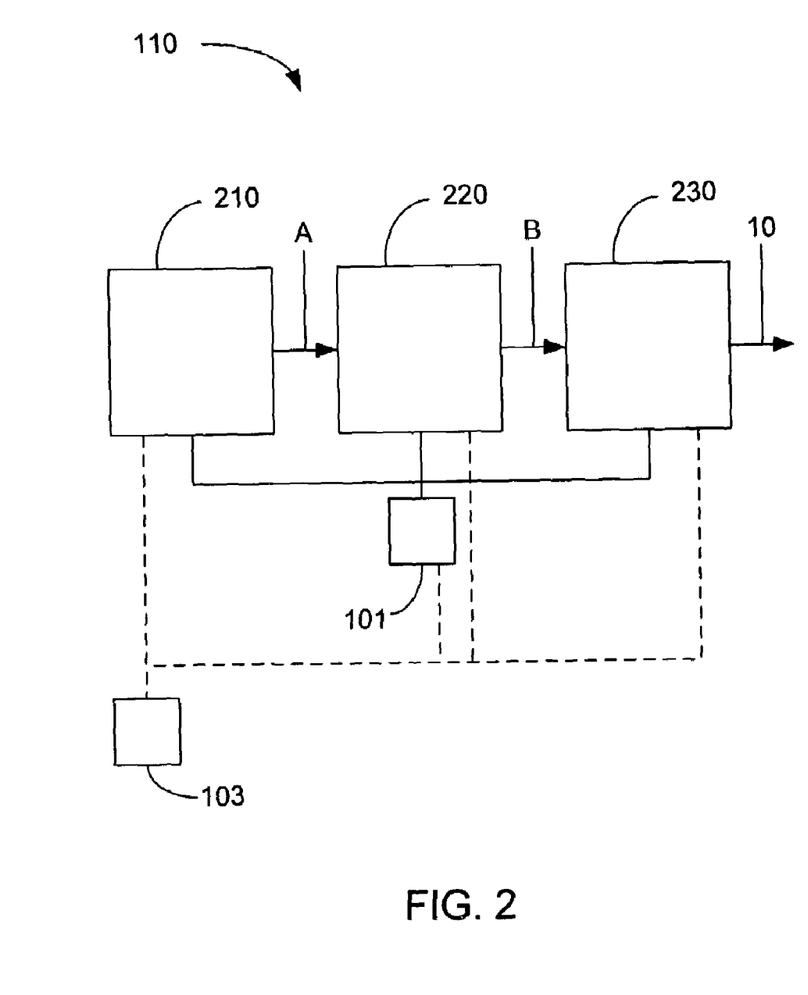
FIG. 2 is a schematic diagram of a preferred embodiment CW light source for a portable BAGI system.

FIG. 2 is a schematic of a preferred embodiment CW light source 110 for a portable BAGI system. Specifically, source 110 includes a light-generating device, or a "seed" light source 210, an OFA 220, and a nonlinear frequency converter 230. Source 210 produces a light beam A that is a seed for optical amplification in OFA 220, which amplifies beam A to produce beam B. Beam B is received as a "pump" beam by converter 230, which uses non-linear optical materials to shift the wavelength of the pump beam to a second wavelength of beam 10. In general, light source 110 is tunable through the adjustment of one or more elements of the light source. In one preferred embodiment, source 210 operates at fixed wavelengths and tuning is effected through changes in converter 230. In other embodiments, seed light source 210 can be tunable or can include two or more separate seed light sources of different wavelength, and converter 230 provides a fixed wavelength shift. In yet another embodiment, both the seed light source 210 and converter 230 are tunable.

Source 110 generates beam 10 composed of light having a narrow spectral distribution, $\Delta v$, centered about a frequency $v$ as follows. Source 210 is preferably a light source that generates light over a small bandwidth, or spread of frequencies $\Delta v_A$ about central frequency $v_A$. For example, source 210 can include, but is not limited to, one or more single-mode or multi-mode solid-state lasers, one or more laser diodes, or some combination of sources. For illustrative purposes, assume that beam A includes light at "n" individual frequencies $v_{Ai}$ with corresponding intensities of $I_{Ai}$.

Amplifier 220 is an optical amplifier having a gain medium and a pump source, as described subsequently, that simultaneously and individually amplifies the n frequencies of beam A to produce beam B having an increased power at each frequency $v_{Ai}$ of $I_{Bi}$. It is preferred that amplifier 220 provides a stable output, providing light at a power and frequency that does not vary appreciably over time. Specifically, it is preferred that the output of amplifier varies by 10% or less for an ambient temperature of from about 0 C to about 40 C. The amplifier output is approximately proportional to absorbed pump power, and thus this requirement is roughly equivalent to a variation of the pump power in the amplifier gain medium of 10% or less. It is also preferred that stable operation of amplifier 220 is provided by air-cooling—that is, that the amplifier components, or any heat sinks attached to the components, are cooled by a flow of the surrounding of air, which may be provide for by a fan, without the use of any intermediate fluids, and furthermore are cooled without any devices, such as thermoelectric coolers (TECs) or other powered cooling or temperature control devices. The use of fiber-based components, such a fiber-based amplifier 220 is preferred and results in a compact, rugged, and electrically efficient BAGI system.

Converter 230, as is also described subsequently, receives the light at the n frequencies, $v_{Ai}$ and powers $I_{Bi}$, and generates light at n different frequencies and powers through nonlinear mixing of light in an optical nonlinear material. For example, the converter input at frequencies $v_{Ai}$ and power $I_{Bi}$ is converted to beam 10 having frequencies $v_i$ and power $I_i$. The spread of frequencies of beam 10 thus reflects the spread of frequencies of beam A, and is preferably within the absorption band of a gas to be imaged.

Figure 3:
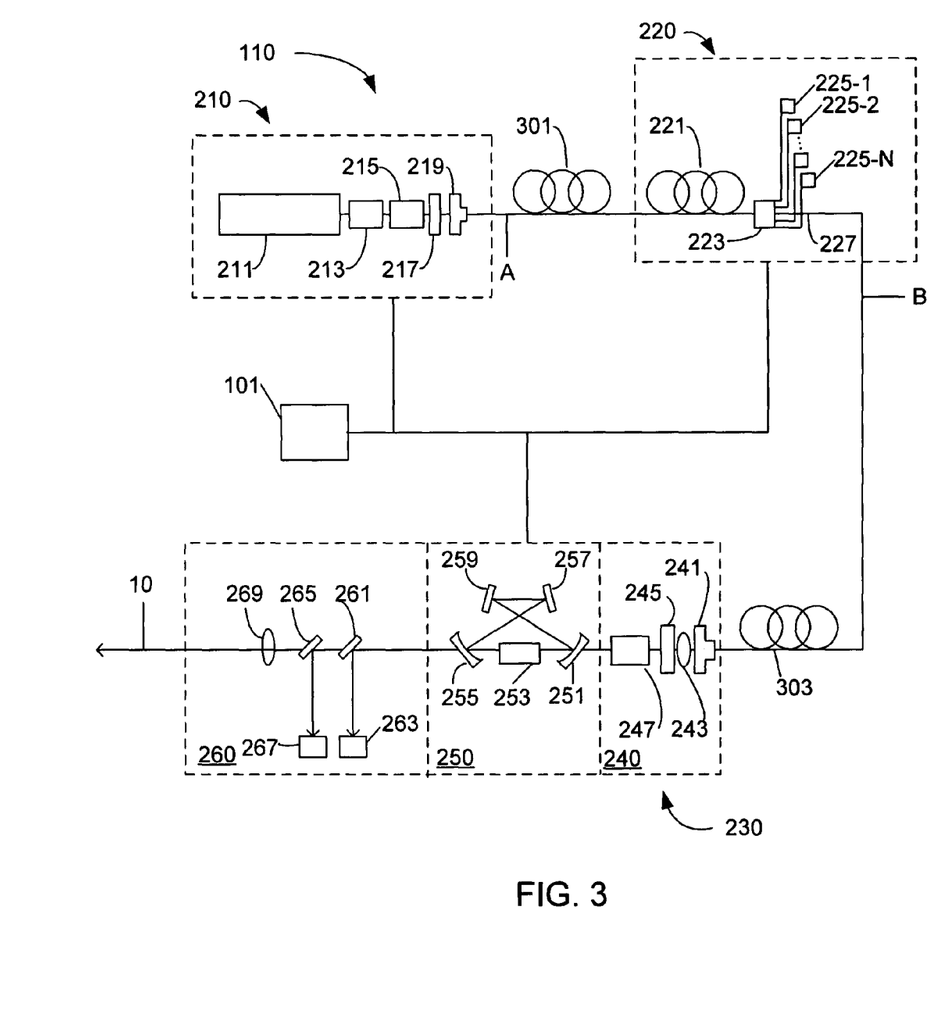
FIG. 3 is a schematic diagram illustrating the details of one preferred light source.

FIG. 3 is a schematic diagram illustrating one preferred light source 110, showing details of a preferred seed light source 210, a preferred amplifier 220, and a preferred converter 230. Source 210 and amplifier 220 are optically coupled through a fiber 301, and amplifier 220 and converter 230 are coupled through a fiber 303.

Source 210 includes a laser 211, Faraday isolators 213 and 215, a half-wave plate 217 and a fiber port 219 providing laser source output A. The polarization state of laser 211 is adjusted by rotating half-wave plate 217, with the output then directed into fiber-port 219, which contains a lens (not shown) to couple the seed radiation of laser 211 into amplifier 220. In a preferred embodiment, laser 211 is a multi-longitudinal-mode Nd:YAG laser having an output of 500 mW at $\lambda_A$ (corresponding to $\nu_A$)=1.0641 μm.

The seed light source 210 output A is amplified by amplifier 220. It is preferred that amplifier 220 is a Ytterbium (Yb)-doped optical fiber amplifier that includes a Yb-doped, double-clad gain fiber 221, N separate pump light sources 225, denoted 225-1 to 225-N, and a tapered coupler 223. Pump light sources 225 are preferably diode light sources. Tapered coupler 223 accepts as input light from pump light sources 225 and provides it into the inner cladding of fiber 221 in a counter-propagating direction relative to output A, which propagates from the core of fiber 221 to the core of the tapered couple and injects it into an output fiber 227. The tapered-fiber coupling approach to pumping fiber lasers and amplifiers is described in U.S. Pat. No. 5,864,644 to DiGiovanni et al.

Amplifier 220 accepts beam A into gain fiber 221 and the output from pump light sources 225 and interacts the light with the Yb-doped fiber to provide amplified output into the single-mode core of fiber 227. Specifically, the double-clad gain fiber 221 serves as the gain medium of amplifier 220, and tapered coupler 223 provides a junction between the multimode fibers connected to pump lasers 225, fiber 221 and fiber 227.

Converter 230 includes input optics 240, an optical parametric oscillator (OPO) 250, and output optics 260. Input optics 240 accept the output beam B from amplifier 220 and provide properly polarized and focused light to OPO 250. Output optics 260 accepts the output of OPO 250, and filters the OPO output to form beam 10.

Input optics 240 include a fiber port 241 adapted to accept beam B, a lens 243, a half-wave plate 245 and a Faraday isolator 247. As described subsequently, half-wave plate 245 and Faraday isolator 247, along with half-wave plate 217 and Faraday isolators 213 and 215, are used to provide the cavity of OPO 250 with properly polarized light and prevent light from back propagation through light source 110.

Figure 4:
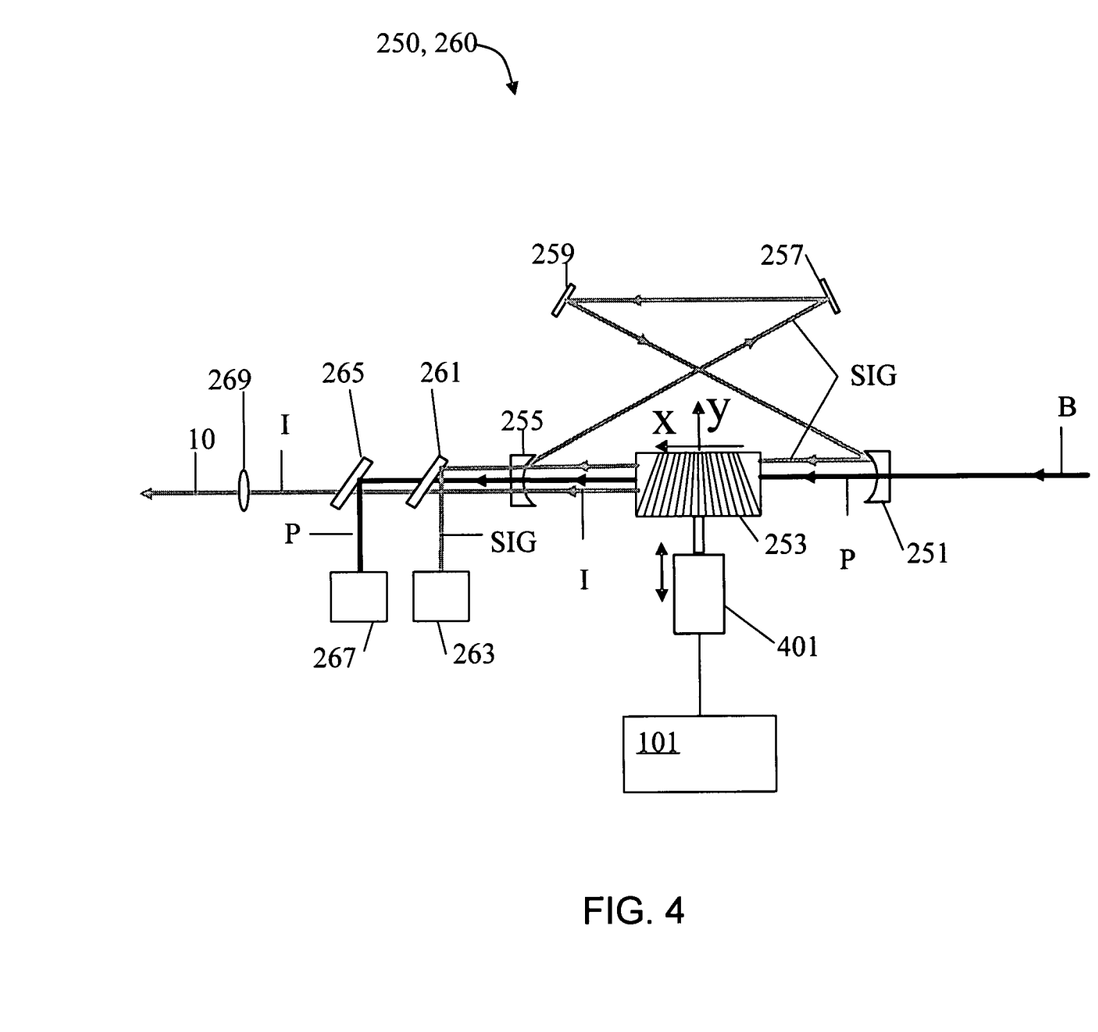
FIG. 4 is a schematic of the preferred embodiment OPO.

OPO 250 and output optics 260 are shown in greater detail in FIG. 4. Amplified beam B enters the cavity of OPO 250 as a pump beam P. OPO 250 includes two curved mirrors 251 and 255, two flat mirrors 257 and 259. OPO 250 also includes as a nonlinear optical material a 50-mm-long PPLN crystal 253 within the optical path and between mirrors 251 and 255. Crystal 253 has nonlinear optical phase-matching properties that result from varying periodicities in the orientation of the crystallographic axis that vary in period from 29.3 to 30.1 μm in a "fan" pattern.

As described subsequently, the output wavelength of OPO 250 is adjusted by moving crystal 253 within the pump beam, which in turn modifies the interaction of the pump with the periodicity of the crystallographic axis to adjust the signal and idler beam wavelengths. The design of OPO cavities of this configuration is described in Bosenberg et al. (Opt. Lett. 21 1336 (1996)). The use of PPLN is described in U.S. Pat. No. 5,434,700 to Yoo, and the construction and use of fan patterned PPLN crystals is described in U.S. Pat. No. 6,359,914 to Powers, et al., incorporated herein by reference.

The cavity of OPO 250 is preferably operated as a singly resonant cavity at the signal wavelength, with cavity mirrors 251, 255, 257, and 259 coated to allow efficient resonance of the corresponding signal while efficiently transmitting the pump and idler beams. Curved mirrors 251 and 255 transmit the majority of light at the pump wavelength $\lambda_A$, which for the preferred light source 210 is the multi-longitudinal-mode output of a Nd:YAG laser at about 1.0641 μm. The wavelengths of the idler and signal beams vary according the periodicity and temperature (nominally 180° C.) of the PPLN crystal in the optical path of the cavity, and can vary between 3.1 and 3.6 μm for the idler and between 1.51 and 1.62 μm for the signal (or frequencies of 2778 to 3226 cm$^{-1}$ for the idler and 6173 to 6623 cm$^{-1}$ for the signal). Alternatively, the system can be tuned to have a signal/idler range of from 1.3 to 4 μm.

Output optics 260 include a pair of dielectric mirrors 261 and 265 and corresponding beam stops 263 and 267 to filter light at the idler frequency from the output of the cavity of OPO 250. Mirror 261 reflects the light at the frequency of pump P, passing light at the frequency of idler I and signal SIG, while mirror 265 reflects light at the frequency of signal SIG, passing light at the frequency of idler I. A lens 269 then collimates the light to form idler I into beam 10, which has a divergence matched to that of the instantaneous field-of-view of the detector in the scanning camera.

In general, OPOs include a nonlinear optical material that interacts with light of a "pump" beam, P, at a pump frequency, $\nu_P$, which is optically converted to a "signal" beam, SIG, having a signal frequency, $\nu_S$, and an "idler" beam, I, having an idler frequency, $\nu_I$. The resonance within the OPO provided by the mirrors results in high power levels of one or more of the beams within the nonlinear material, which in turn more efficiently generates signal and idler beams. The operational threshold of the OPO is the pump power at which the gain in signal wave per pass of the cavity exceeds the loss at that frequency. Operation at a pump power that is suitably above the threshold results in significant conversion of the pump wave to the output waves.

The pump, signal, and idler frequencies are related through the conservation of energy. Specifically, the energy of a particular photon is proportional to the photon's frequency. The energy of a pump photon is equal to the sum of the energies of the generated signal and idler photons, or, in terms of photon frequency: $\nu_P = \nu_I + \nu_S$. Since wavelength and frequency of light are related through $\nu = c/\lambda$, where c is the speed of light, the pump wavelength, $\lambda_P$, idler wavelength, $\lambda_I$, and signal wavelength, $\lambda_S$, are related by: $1/\lambda_P = 1/\lambda_I + 1/\lambda_S$.

It is preferred that the idler beam I is provided as beam 10. In particular, since the pump beam of OPO 250 includes two or more wavelengths (frequencies) corresponding to the output of light source 210, beam 10 is also multi-wavelength, and includes one idler wavelength for each pump wavelength.

In the preferred embodiment, OPO 250 includes tuning over a range of wavelengths, λ, that is useful for matching the absorption bands of various gases. As shown in FIG. 4, OPO 250 includes a translator 401 that is manually controlled by the operator. Controlling the position of crystal 253 within pump beam P adjusts the periodicity of the PPLN crystal, thus adjusting the wavelengths of the signal and idler beams.

Tuning through the movement of crystal 253 is achieved as follows. Crystal 253 is aligned for propagation of pump beam P along the x-axis, with periods varying along the y-axis from 29.3 to 30.1 μm. The period of the crystal can be adjusted by moving the crystal along the y-axis and relative to pump beam P, producing non-linear interactions that change the frequency of the signal and idler beam as a function of the position of the crystal along the y-axis. Tuning using the fan-shaped PPLN crystal 253 is accomplished by manually moving the crystal in the "y" direction as indicated in FIG. 4 shown by translator 401. This could, eventually, be controlled by computer 101. Translator 401 can be a stepper motor or any other mechanism for repeatably and controllably translating crystal 253. PPLN crystal 253 has a theoretical tuning range at 180° C. of about 350 cm$^{-1}$, and can convert pump beam P having a wavelength $\lambda_P=\lambda_A$ of 1.06 μm into a signal beam (beam SIG) having a wavelength $\lambda_S$ that is adjustable from 1.53 to 1.62 μm (frequency $v_S$ of 6173 to 6536 cm$^{-1}$) and an idler beam (beam I) having a wavelength $\lambda_I$ that is adjustable from 3.1 to 3.5 μm (frequency 2857 to 3226 cm$^{-1}$). Translating crystal 253 approximately 0.04 mm moves the OPO gain peak approximately 4 cm$^{-1}$.

The operation of OPO 250 is polarization dependent, requiring a pump beam that is linearly polarized along the z-axis of the PPLN crystal 253, that is, in a direction perpendicular to the plane of FIG. 2. The proper polarization is achieved using Faraday isolators 213 and 215 and half-wave plate 217, and half-wave plate 245 and Faraday isolator 247, which also isolates the amplifier 220 from the cavity of OPO 250.

In alternative embodiments of OPO 250, other tuning elements may be placed within the optical path of the pump, signal, or idler beams within the OPO to modify the tuning characteristics of the cavity, as is known in the art. Examples of other tuning elements include, but are not limited to moving the various mirrors to increase or decrease the path length through the cavity, or inserting air or rotating, solid etalons within the cavity.

In another embodiment, the spacing and coating of one or more of mirrors 251, 255, 257, and 259 are modified so that OPO 250 resonates at a different frequency, such as that of the idler beam, or is doubly resonant and oscillates in both the signal and idler beam frequencies. The mirrors could also be coated to simultaneously resonate both the pump and idler beam or the pump and the signal beam, thus resonating the pump in the cavity and lowering the threshold of the OPO.

There are several features of light source 110 that provide for stable light source power and frequency, improved tuning range and power, reduced power consumption, and easy serviceability, described below with reference to the above described source 210, amplifier 220, and converter 230. Alternative embodiments that exhibit these features are possible and will become apparent upon consideration of the following.

One characteristics of fiber amplifiers is that amplification is limited by phenomena parasitic loss mechanisms such as stimulated Brilliion scattering (SBS). SBS results in the coupling of a portion of the amplified output wave into a spectrally-shifted, backward-propagating beam, a loss of forward power, and instabilities within the amplifier that can lead to damage of the pump diodes or of the fiber. SBS occurs above a threshold power level, limiting the maximum amount of output power of a fiber amplifier. A conflicting characteristic of OPOs is that they have a power threshold that must be exceeded to produce frequency shifted light. Both SBS and the power threshold of OPOs are determined by the specific configuration and materials of the amplifier and OPO. It is thus seen that there are trade-offs in the design of a tunable light source that need to be addressed.

These trade-offs are effectively addressed by the use of source 210, amplifier 220, and converter 230, as follows. The SBS threshold energy applies for each frequency of amplified light that is within a characteristic SBS interaction bandwidth. As photons at $v_P$ travel the length of the fiber, some are scattered by SBS to form photons at $v_P$-$v_{SBS}$. Photons at the new frequency can interact with the pump photons via the SBS coupling to create more photons at the new frequency. Thus, the new frequency can grow rapidly to significantly deplete the forward propagating wave and cause a disruptive backward wave. By providing seed light at more than one frequency the amplifier power at which the onset of SBS occurs can be increased. This is a result of the fact that there is a finite bandwidth ($\Delta v_{SBS}$) for the SBS interaction. As a simplified example, providing amplifier input at two nearby frequencies (but with a separation greater than $\Delta v_{SBS}$) each with the same SBS threshold energy and amplification factor allows for a doubling of the total amplified power. This occurs because the separation between the two frequencies is wider than $\Delta v_{SBS}$; thus, shifted photons from one of the frequencies cannot interact with the other frequency and vice-versa. Source 210 preferably produces light at more than one frequency that cannot interact with each other via SBS and that have a sufficiently narrow envelope to produce an idler beam that is spectrally narrower than the gas to be detected. More specifically, light source 210 is operated so that no one of the intensities $I_i$ is greater that the SBS threshold power at $v_i$. Since each frequency $v_i$ can be individually amplified in amplifier 220, the total power of beam B is greater than if the output from single mode laser source had been used.

In addition, the short gain region of amplifier 220 increases the SBS threshold energy. Specifically, the tapered-fiber configuration of amplifier 220 amplifies over a short gain region. Amplifier 220 is also preferably operated in a counter-propagating operation, where light from pump lasers 225 and light from laser source 221 are provided to tapered coupler in opposite directions. Counter-propagating operation also serves to increase the SBS threshold by minimizing the length of fiber through which high power radiation must travel.

In addition, the tapered-fiber coupling approach is more amenable to replacement of individual pump lasers, and thus provides a BAGI system that is less expensive to repair since the failure of an individual pump laser can be repaired by replacing the failed laser, and not by replacing the entire amplifier.

As an example of the improved performance obtained with the preferred embodiment, laser source 211 produces a beam A having n=4 separate output wavelengths with a total laser output power of 500 mW. Amplifier 220 has six, 915 nm pump diodes in a counter-propagating configuration and a gain region length of 8 meters. Amplifier 220 produces 10 Watts of output power without inducing SBS. OPO 250 accepts a pump power of 10 W of output power from amplifier 220 and emits between 400 and 500 mW of idler output. In contrast, the amplified output of a single-frequency laser light source is reduced to 4 to 5 W due to SBS. Thus the use of several modes allows for a doubling of the output power of the amplifier The ability to operate BAGI system 100 is aided by the lower power consumption of amplifier 220. Prior art amplifiers for BAGI systems use 975 nm pump lasers. Pumping at 975 nm is an optically efficient choice for a pump laser because the Yb absorption is strong at that wavelength. However, the Yb absorption is also spectrally narrow, requiring a pump with an output frequency that does not drift during the operation of the amplifier. With the diode pump lasers of the prior art, the heating of the pump laser during normal operation causes a frequency drift that results in an unacceptable loss of power. It is not possible to sufficiently control the temperature of pump lasers operating at 975 nm using heat sinks and fans, and thus prior art amplifiers for BAGI systems operating at 975 use active temperature control devices, such as TECs, to maintain a constant output power. The use of active temperature control devices results in a high electrical power demand and in difficulties associated with active power control that result in variations of output power and thermal runaway of the TECs.

In the preferred embodiment, amplifier 220 includes pump light sources 225 that have an output wavelength that vary with the operational temperature of the pump, but where the fraction of pump light absorbed in gain medium of fiber 221 does not vary significantly. In one embodiment, the pump diode wavelength is selected so that it tunes over a portion of the rare-earth ion absorption spectrum whose amplitude changes by no more than 10% over the expected temperature range, resulting in a variation in output power of no more than 10%, over an ambient temperature of about 0 C to about 40 C. Changes in the pump wavelength will thus not have a large effect on the output power of the ampler. In one embodiment, for example, a Yb-doped fiber 221 is pumped with a pump source 225 having an nominal output at a wavelength of 915 nm. The Yb absorption feature at 915 nm is quite broad and, thus, is relatively flat and insensitive to changes in the pump diode wavelength. As used herein, the term "relatively flat region" refers to a portion of the absorption spectrum of the fiber gain medium having small changes with wavelength over some range of wavelengths. As a result of the absorption spectrum having a relatively flat region that includes the range of pump output, the absorption of the pump radiation by the fiber is nearly complete over a range of wavelengths that might be emitted by the pump diode, independent of the operating conditions, such as temperature, of the pump diode. The relatively flat absorption feature results in a relatively flat gain variation with pump wavelength. It is thus not necessary to maintain extreme temperature control of pump source 225 to provide stable output of such an amplifier.

The benefit of pumping at a wavelength within the relatively flat absorption regions of the gain medium, is that, for a gas imaging instrument, the amplifier can be operated without active temperature control of the pump diodes. Because such control can result in significant electrical power consumption, its elimination can make the gas imaging instrument significantly more efficient. If the pump diodes are selected to emit an appropriate wavelength near 915 nm when they are at their steady state operating temperature, the absorption of the diode pump light by the amplifier will be near complete over a wide range of ambient temperatures. Thus, it is not necessary to actively control the pump diode temperature. More specifically, when using a 915 nm pump source, amplifier 220 requires only air-cooling—that is movement of the surrounding air about the amplifier, or heat sinks on the amplifier, to provide cooling, without the need for active temperature control components, such as TECs, are required for cooling the pump lasers. The net electrical requirement, including the power to operate the pump lasers and the power to cool the lasers is markedly less than the power requirement for 975 nm pumped amplifiers.

In addition, since amplifier 220 does not require active control using TECs, there are no thermal runaway problems as experienced with prior amplifiers.

As an example of the operation of amplifier 220, preferred BAGI system 100 was tested in an environmental chamber at temperatures ranging from 15 C to 40 C. No variation in output power was noted over this temperature range. The preferred BAGI system was then compared to a system having an amplifier operating at 975 nm. Despite the additional power required to drive the extra pump diodes, the total power requirement of the inventive amplifier decreased due to the elimination of the TECs. The total BAGI system power requirement for a system having 975 nm pump sources was about 240 W, while the total power requirement for BAGI system 100 was about 160 W.

As an alternative embodiment amplifier 220, the gain medium absorbs nearly all of the output from pump lasers 225 over the operational temperature range of the pump lasers. This can be accomplished, for example, with a fiber gain medium that is either long enough, while avoiding SBS, or that has a high enough absorbing species concentration to absorb a significant portion of the input pump light. Variations in the output wavelength of the pump lasers will thus not affect the gain of amplifier 220.

One benefit of the high optical output of amplifier 220 is improved performance and reliability of converter 230. As noted previously, crystal 253 requires a threshold of power to generate beam 10, and also requires some amount above the threshold to operate stably. The inventive laser source 210 and amplifier 220 provide power to beam B that is approximately 2.5–3.3 times the threshold. This power level provides for reliable operation of OPO 250. In addition, higher operating powers result in stable operation that was less dependent on the crystal and coating quality, which in turn increases the yield of acceptable crystals, and improved tuning range.

As one example of a preferred embodiment BAGI system 100, laser 211 is a CW seed laser, such as an Nd-based laser, emitting about 4 modes each having a narrow spectral output of less than about 100 MHz width near 1064 nm, and a total (all modes) output power of approximately 500 mW. Amplifier 220 preferably has six pump diodes (N=6) and provides 24 W of pump power to produce approximately 10 W of output power at a wavelength of 1064 nm from a laser 211 seed input provided into the fiber of 300–400 mW. This output from amplifier 220 is more than 2.3 times the power required for stable operation of OPO 250.

Alternative Embodiments

There are several embodiments of light source 110 that are within the scope of the present invention. Tuning of beam 10 can result from tuning one or more of the elements of light source 110. Thus, for example, a fixed-wavelength light seed 210 can be coupled with a tunable non-linear material of converter 230, a wavelength tunable light seed, adjustable through the control of computer 101, can be coupled with a fixed non-linear material of the OPO, and two or more fixed-wavelength light seeds of different wavelengths can provide light to a fixed-wavelength or a wavelength tunable OPO. When tuning wavelengths, it is preferable that the tuning occurs in a time that is less than the scanning time of a pixel of camera 131. Thus, for example, a wavelength tunable seed laser that produces an output that dithers between two wavelengths on alternate camera scans can be used to produce alternating images at the two wavelengths.

Figure 5:
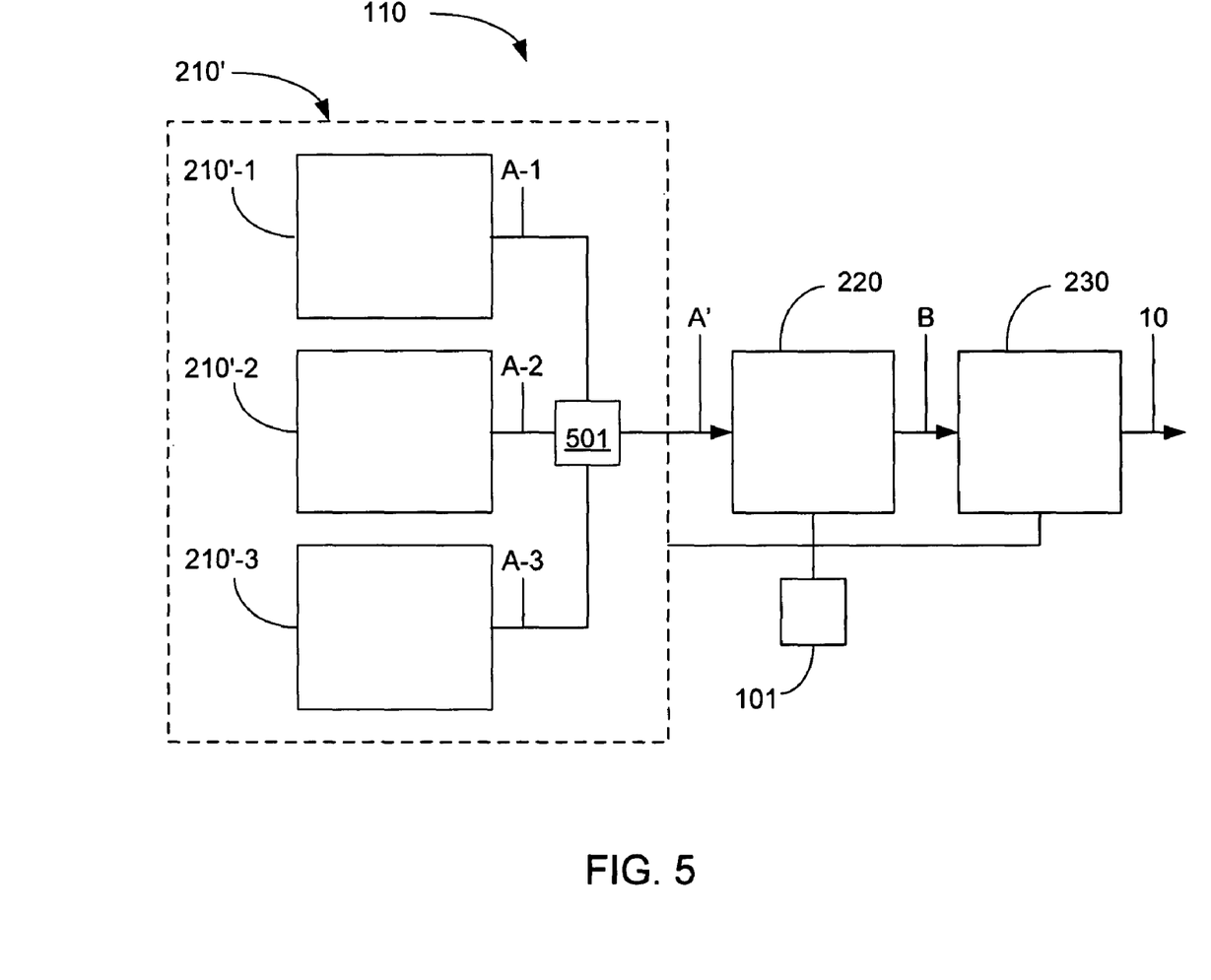
FIG. 5 is a schematic diagram of an alternative embodiment light source.

An example of an alternative embodiment light source with two or more separate light sources is illustrated in the schematic diagram of FIG. 5. An alternative seed light source 210' as shown in FIG. 5 can include three, separate light sources 210, as described previously, that each generate one of beam A-1, A-2, or A-3. Source 210' also includes a computer controlled optical switch 501 that discriminates or selects from among the three beams (A-1, A-2, and A-3), and directs one of these as beam A' into amplifier 220.

Many other embodiments are within the scope of the present invention. Embodiments of light seed source 210 include, but are not limited to, a solid-state laser, such as a Nd:YAG laser, or a diode light source. Embodiments of amplifier 220 include, but are not limited to, a fiber-amplifier employing a fused and tapered fiber bundle, one or more V-groove elements for coupling amplifier pump laser light into the amplifier, and the use of polarization maintaining gain fiber. Embodiments of OPO 250 include, but are not limited to, OPOs that are singly resonant with either the signal or the pump beams, or that are doubly resonant with the signal and pump beams.

Other embodiments within the scope of the present invention include replacing light seed 210 and amplifier 220 with a sufficiently narrow fiber laser pump or fiber Raman laser pump, replacing the amplifier with a fiber Raman laser pump, the use of a fiber Raman amplifier or fiber amplifier within light source 110, and an OPO that is a waveguide PPLN OPO. The OPO can also use other quasi-phase-matched nonlinear crystals to access similar or different wavelength ranges for gas imaging. Such crystals include periodically-poled potassium titanyl phosphate ($KTiOPO_4$, or KTP), potassium titanyl arsenate ($KTiOAsO_4$, or KTA), lithium tantalate, Rubidium titanyl arsenate ($RbTiOAsO_4$, or RTA), and GaAs. The last crystal is particularly interesting to allow tuning at longer wavelengths. Alternate embodiments also include the use of birefringently-phasematched nonlinear materials in the frequency converter, and nonlinear converters that are not OPOs, such as difference-frequency generators or Raman shifters.

The present invention includes a light source of a BAGI system that provides for a portable device for remotely detecting a variety of gases. The embodiments described above are illustrative of the present invention and are not intended to limit the scope of the invention to the particular embodiments described. Accordingly, while one or more embodiments of the invention have been illustrated and described, it will be appreciated that various changes can be made therein without departing from the spirit or essential characteristics thereof. For example, while the present invention describes the use of 915 nm pump lasers in an amplifier, other pump wavelengths may also result in an amplifier that does not need active cooling. Accordingly, the disclosures and descriptions herein are intended to be illustrative, but not limiting, of the scope of the invention, which is set forth in the following claims.

What is claimed is:

1. A light source to provide illumination for a scene for a backscatter absorption gas imaging system comprising:
    a light-generating device producing light at more than one wavelength;
    an optical fiber amplifier having at least one pump laser with an output and a gain medium, where each of said at least one pump laser is an air-cooled pump laser having an operating temperature at an ambient temperature, where said optical fiber amplifier accepts light from said light generating device and produces amplified light at said more than one wavelength, and where the absorption of the output of said pump laser by said gain medium varies by no more than about 10% over a range of ambient temperatures of from about 0 C to about 40 C; and
    a nonlinear frequency converter including an optical parametric oscillator (OPO) to accept said amplified light and generate an output of the light source at wavelengths shifted from and corresponding to each of said more than one wavelength.

2. The light source of claim 1, wherein said light-generating device produces continuous-wave light.

3. The light source of claim 1, wherein said light-generating device produces quasi-continuous-wave light, where said quasi-continuous-wave light has a repetition rate greater than about 10 kHz.

4. The light source of claim 1, wherein said light-generating device is a multi-longitudinal-mode laser.

5. The light source of claim 4, wherein said laser is a Nd:YAG laser.

6. The light source of claim 1, wherein said light-generating device is laser diode.

7. The light source of claim 1, wherein said light-generating device is fiber diode.

8. The light source of claim 1, wherein said light-generating device includes two or more light-generating devices; and further including a switch to select light from one of said two or more light-generating devices for acceptance by said optical fiber amplifier.

9. The light source of claim 1, wherein said light-generating device produces wavelength tunable light.

10. The light source of claim 9, wherein said wavelength tunable light is tunable between two wavelengths.

11. The light source of claim 1, wherein said optical fiber amplifier is a Yb-doped, tapered fiber amplifier.

12. The light source of claim 11, wherein said pump laser wavelength is near 915 nm.

13. The light source of claim 1, wherein said OPO has a cavity that tunably adjusts said wavelength output.

14. The light source of claim 1, wherein said OPO, having accepted said amplified light, generates a signal beam and an idler beam, and wherein said OPO is singly resonant at the wavelength of either said signal beam or of said idler beam.

15. The light source of claim 1, wherein said OPO, having accepted said amplified light, generates a signal beam and an idler beam, and wherein said OPO is doubly resonant at the wavelength of said signal beam and at the wavelength of said idler beam.

16. The light source of claim 1, wherein said OPO, having accepted said amplified light, generates a signal beam and an idler beam, further including optics to provide said idler beam as said adjustable wavelength output.

17. A light source to provide illumination for a scene for a backscatter absorption gas imaging system comprising:
    a light-generating device producing light at more than one wavelength;
    an optical fiber amplifier to accept light from said light-generating device and produce amplified light at said more than one wavelength, wherein said optical fiber amplifier is a Yb-doped, tapered optical fiber amplifier, wherein said optical fiber amplifier includes at least one pump laser and a gain medium, and wherein each of said at least one pump laser is an air-cooled pump laser having an operating temperature at an ambient temperature; and
    a nonlinear frequency converter including an optical parametric oscillator (OPO) to accept said amplified light and generate an output of the light source at wavelengths shifted from and corresponding to each of said more than one wavelength.

18. The light source of claim 17, wherein said air-cooled pump laser has an operating temperature at an ambient temperature, and wherein the absorption of the output of said pump laser by said gain medium varies by no more than about 10% over a range of said ambient temperatures of from about 0 C to about 40 C.

19. The light source of claim 17, wherein said light-generating device produces continuous-wave light.

20. The light source of claim 17, wherein said light-generating device produces quasi-continuous-wave light, where said quasi-continuous-wave light has a repetition rate greater than about 10 kHz.

21. The light source of claim 17, wherein said light-generating device is a multi-longitudinal-mode laser.

22. The light source of claim 21, wherein said laser is a Nd:YAG laser.

23. The light source of claim 17, wherein said light-generating device is a laser diode.

24. The light source of claim 17, wherein said light-generating device is a fiber diode.

25. The light source of claim 17, wherein said light-generating device includes two or more light-generating devices; and further including switch to select light from one of said two or more light-generating devices for acceptance by said optical fiber amplifier.

26. The light source of claim 17, wherein said light-generating device produces wavelength tunable light.

27. The light source of claim 26, wherein said wavelength tunable light is tunable between two wavelengths.

28. The light source of claim 17, wherein said optical fiber amplifier includes at least one pump laser with an output of near 915 nm.

29. The light source of claim 17, wherein said OPO has a cavity that tunably adjusts said wavelength output.

30. The light source of claim 17, wherein said OPO, having accepted said amplified light, generates a signal beam and an idler beam, and wherein said OPO is singly resonant at the wavelength of either said signal beam or of said idler beam.

31. The light source of claim 17, wherein said OPO, having accepted said amplified light, generates a signal beam and an idler beam, and wherein said OPO is doubly resonant at the wavelength of said signal beam and at the wavelength of said idler beam.

32. The light source of claim 17, wherein said OPO, having accepted said amplified light, generates a signal beam and an idler beam, further including optics to provide said idler beam as said adjustable wavelength output.

33. A light source to provide illumination for a scene for a backscatter absorption gas imaging system comprising:
two or more light-generating devices each producing light at more than one wavelength;
a switch to select light from one of said two or more light-generating devices;
an optical fiber amplifier to accept said selected light and produce amplified light at the more than one wavelength of said selected light; and
an optical parametric oscillator (OPO) to accept said amplified light and generate an output of the light source at wavelengths shifted from and corresponding to each of said more than one wavelength.

34. The light source of claim 33, wherein said light-generating device produces continuous-wave light.

35. The light source of claim 33, wherein said light-generating device produces quasi-continuous-wave light, where said quasi-continuous-wave light has a repetition rate greater than about 10 kHz.

36. The light source of claim 33, wherein at least one of said two or more light-generating devices is a multi-mode laser.

37. The light source of claim 36, wherein said laser is a Nd:YAG laser.

38. The light source of claim 33, wherein at least one of said two or more light-generating devices is a laser diode.

39. The light source of claim 33, wherein at least one of said two or more light-generating devices produces tunable light.

40. The light source of claim 33, wherein said optical fiber amplifier is a Yb-doped, tapered fiber amplifier.

41. The light source of claim 33, wherein said optical fiber amplifier includes at least one pump laser with an output of near 915 nm.

42. The light source of claim 33, wherein said OPO, having accepted said amplified light, generates a signal beam and an idler beam, and wherein said OPO is singly resonant at the wavelength of either said signal beam or of said idler beam.

43. The light source of claim 33, wherein said OPO, having accepted said amplified light, generates a signal beam and an idler beam, and wherein said OPO is doubly resonant at the wavelength of said signal beam and at the wavelength of said idler beam.

44. The light source of claim 33, wherein said OPO, having accepted said amplified light, generates a signal beam and an idler beam, further including optics to provide said idler beam as said adjustable wavelength output.

45. A light source to provide illumination for a scene for a backscatter absorption gas imaging system comprising:
a diode-pumped fiber laser producing an output of light at more than one wavelength, where said diode-pumped fiber laser is an air-cooled laser having an operating temperature at an ambient temperature, and where said output varies with temperature; and
a nonlinear frequency converter including an optical parametric oscillator (OPO) to accept said output and generate an output of the light source at wavelengths shifted from and corresponding to each of said more than one wavelength;
where said diode-pumped fiber laser is sufficiently air-cooled to provide an output hat varies by no more than 10% over an ambient temperature range of from about 0 C to about 40 C.

46. A backscatter absorption gas imaging system operating at an ambient temperature for imaging a gas between the system and a scene, comprising:
a light source to generate an output for illuminating said scene, including
a light-generating device producing light at more than one wavelength,
an optical fiber amplifier having at least one pump laser with an output and a gain medium, where each of said at least one pump laser is an air-cooled pump laser having an operating temperature at said ambient temperature, where said optical fiber amplifier accepts light from said light generating device and produces amplified light at said more than one wavelength, and where the absorption of the output of said pump laser by said gain medium varies by no more than about 10% over an ambient temperature range of from about 0 C to about 40 C; and a nonlinear frequency converter including an optical parametric oscillator (OPO) to accept said amplified light and generate an output of the light source at wavelengths shifted from and corresponding to each of said more than one wavelength; and a camera responsive to backscattered illumination by said light source.

47. The backscatter absorption gas imaging system of claim 46, wherein said light-generating device produces continuous-wave light.

48. The backscatter absorption gas imaging system of claim 46, wherein said light-generating device produces quasi-continuous-wave light, where said quasi-continuous-wave light has a repetition rate greater than about 10 kHz.

49. The backscatter absorption gas imaging system of claim 46, wherein said light-generating device is a multi-longitudinal-mode laser.

50. The backscatter absorption gas imaging system 49, wherein said laser is a Nd:YAG laser.

51. The backscatter absorption gas imaging system of claim 46, wherein said light-generating device is laser diode.

52. The backscatter absorption gas imaging system of claim 46, wherein said light-generating device is fiber diode.

53. The backscatter absorption gas imaging system of claim 46, wherein said light-generating device includes two or more light-generating devices; and further including a switch to select light from one of said two or more light-generating devices for acceptance by said optical fiber amplifier.

54. The backscatter absorption gas imaging system of claim 46, wherein said light-generating device produces wavelength tunable light.

55. The backscatter absorption gas imaging system of claim 54, wherein said wavelength tunable light is tunable between two wavelengths.

56. The backscatter absorption gas imaging system of claim 46, wherein said optical fiber amplifier is a Yb-doped, tapered fiber amplifier.

57. The backscatter absorption gas imaging system of claim 56, wherein said pump laser wavelength is near 915 nm.

58. The backscatter absorption gas imaging system of claim 46, wherein said OPO has a cavity that tunably adjusts said wavelength output.

59. The backscatter absorption gas imaging system of claim 46, wherein said OPO, having accepted said amplified light, generates a signal beam and an idler beam, and wherein said OPO is singly resonant at the wavelength of either said signal beam or of said idler beam.

60. The backscatter absorption gas imaging system of claim 46, wherein said OPO, having accepted said amplified light, generates a signal beam and an idler beam, and wherein said OPO is doubly resonant at the wavelength of said signal beam and at the wavelength of said idler beam.

61. The backscatter absorption gas imaging system of claim 46, wherein said OPO, having accepted said amplified light, generates a signal beam and an idler beam, further including optics to provide said idler beam as said adjustable wavelength output.

62. A backscatter absorption gas imaging system operating at an ambient temperature for imaging a gas between the system and a scene, comprising:

a light source to generate an output for illuminating said scene, including a light-generating device producing light at more than one wavelength, an optical fiber amplifier to accept light from said light-generating device and produce amplified light at said more than one wavelength, wherein said optical fiber amplifier is a Yb-doped, tapered optical fiber amplifier, wherein said optical fiber amplifier includes at least one pump laser, and wherein each of said at least one pump laser is an air-cooled pump laser, and a nonlinear frequency converter including an optical parametric oscillator (OPO) to accept said amplified light and generate an output of the light source at wavelengths shifted from and corresponding to each of said more than one wavelength; and a camera responsive to backscattered illumination by said light source.

63. The backscatter absorption gas imaging system of claim 62, wherein said air-cooled pump laser has an operating temperature at an ambient temperature, and wherein the absorption of the output of said pump laser by said gain medium varies by no more than about 10% over an ambient temperature range of from about 0 C to about 40 C.

64. The backscatter absorption gas imaging system of claim 62, wherein said light-generating device produces continuous-wave light.

65. The backscatter absorption gas imaging system of claim 62, wherein said light-generating device produces quasi-continuous-wave light, where said quasi-continuous-wave light has a repetition rate greater than about 10 kHz.

66. The backscatter absorption gas imaging system of claim 62, wherein said light-generating device is a multi-longitudinal-mode laser.

67. The backscatter absorption gas imaging system of claim 66, wherein said laser is a Nd:YAG laser.

68. The backscatter absorption gas imaging system of claim 62, wherein said light-generating device is a laser diode.

69. The backscatter absorption gas imaging system of claim 62, wherein said light-generating device is a fiber diode.

70. The backscatter absorption gas imaging system of claim 62, wherein said light-generating device includes two or more light-generating devices; and further including a switch to select light from one of said two or more light-generating devices for acceptance by said optical fiber amplifier.

71. The backscatter absorption gas imaging system of claim 62, wherein said light-generating device produces wavelength tunable light.

72. The backscatter absorption gas imaging system of claim 71, wherein said wavelength tunable light is tunable between two wavelengths.

73. The backscatter absorption gas imaging system of claim 62, wherein said optical fiber amplifier includes at least one pump laser with an output of near 915 nm.

74. The backscatter absorption gas imaging system of claim 62, wherein said OPO has a cavity that tunably adjusts said wavelength output.

75. The light source of claim 62, wherein said OPO, having accepted said amplified light, generates a signal beam and an idler beam, and wherein said OPO is singly resonant at the wavelength of either said signal beam or of said idler beam.

76. The backscatter absorption gas imaging system of claim 62, wherein said OPO, having accepted said amplified light, generates a signal beam and an idler beam, and wherein said OPO is doubly resonant at the wavelength of said signal beam and at the wavelength of said idler beam.

77. The backscatter absorption gas imaging system of claim 62, wherein said OPO, having accepted said amplified light, generates a signal beam and an idler beam, further including optics to provide said idler beam as said adjustable wavelength output.

78. A backscatter absorption gas imaging system for imaging a gas between the system and a scene, comprising:
a light source to generate an output for illuminating said scene, including
two or more light-generating devices each producing continuous-wave light at more than one wavelength;
a switch to select light from one of said two or more light-generating devices;
an optical fiber amplifier to accept said selected light and produce amplified light at the more than one wavelength of said selected light; and
an optical parametric oscillator (OPO) to accept said amplified light and generate an output of the light source at wavelengths shifted from and corresponding to each of said more than one wavelength; and
a camera responsive to backscattered illumination by said light source.

79. The backscatter absorption gas imaging system of claim 78, wherein said light-generating device produces continuous-wave light.

80. The light source of claim 78, wherein said light-generating device produces quasi-continuous-wave light, where said quasi-continuous-wave light has a repetition rate greater than about 10 kHz.

81. The light source of claim 78, wherein at least one of said two or more light-generating devices is a multi-mode laser.

82. The light source of claim 81, wherein said laser is a Nd:YAG laser.

83. The light source of claim 78, wherein at least one of said two or more light-generating devices is a laser diode.

84. The light source of claim 78, wherein at least one of said two or more light-generating devices produces tunable light.

85. The light source of claim 78, wherein said optical fiber amplifier is a Yb-doped, tapered fiber amplifier.

86. The light source of claim 78, wherein said optical fiber amplifier includes at least one pump laser with an output of near 915 nm.

87. The light source of claim 78, wherein said OPO, having accepted said amplified light, generates a signal beam and an idler beam, and wherein said OPO is singly resonant at the wavelength of either said signal beam or of said idler beam.

88. The light source of claim 78, wherein said OPO, having accepted said amplified light, generates a signal beam and an idler beam, and wherein said OPO is doubly resonant at the wavelength of said signal beam and at the wavelength of said idler beam.

89. The light source of claim 78, wherein said OPO, having accepted said amplified light, generates a signal beam and an idler beam, further including optics to provide said idler beam as said adjustable wavelength output.

90. A backscatter absorption gas imaging system for imaging a gas between the system and a scene, comprising:
a light source to provide illumination for a scene for a backscatter absorption gas imaging system comprising
a diode-pumped fiber laser producing an output of light at more than one wavelength, where said diode-pumped fiber laser is an air-cooled laser, and where said output varies with temperature, and
a nonlinear frequency converter including an optical parametric oscillator (OPO) to accept said output and generate an output of the light source at wavelengths shifted from and corresponding to each of said more than one wavelength; and
a camera responsive to backscattered illumination by said light source,
where said diode-pumped fiber laser is sufficiently air-cooled to provide an output that varies by no more than 10% over an ambient temperature range of from about 0 C to about 40 C.

* * * * *

UNITED STATES PATENT AND TRADEMARK OFFICE
CERTIFICATE OF CORRECTION

| | | |
|---|---|---|
| PATENT NO. | : 7,151,787 B2 | |
| APPLICATION NO. | : 10/658906 | |
| DATED | : December 19, 2006 | |
| INVENTOR(S) | : Kulp et al. | |

It is certified that error appears in the above-identified patent and that said Letters Patent is hereby corrected as shown below:

Col. 17,
Claim 25, Line 25, after "including" insert -- a --
Col. 18,
Claim 45, Line 47, change "hat" to --that--

Signed and Sealed this

Thirteenth Day of March, 2007

JON W. DUDAS
*Director of the United States Patent and Trademark Office*